United States Patent
Lee et al.

(10) Patent No.: US 9,731,882 B2
(45) Date of Patent: Aug. 15, 2017

(54) ORAL CARE KIT FOR DISPLAYING A PORTION OF A TOOTHBRUSH

(75) Inventors: David K. Lee, East Brunswick, NJ (US); Quang Nguyen, Hillsborough, NJ (US)

(73) Assignee: COLGATE-PALMOLIVE COMPANY, New York, NY (US)

(*) Notice: Subject to any disclaimer, the term of this patent is extended or adjusted under 35 U.S.C. 154(b) by 0 days.

(21) Appl. No.: 14/117,968

(22) PCT Filed: May 27, 2011

(86) PCT No.: PCT/US2011/038297
§ 371 (c)(1),
(2), (4) Date: Nov. 15, 2013

(87) PCT Pub. No.: WO2012/166085
PCT Pub. Date: Dec. 6, 2012

(65) Prior Publication Data
US 2014/0083885 A1    Mar. 27, 2014

(51) Int. Cl.
*B65D 75/36* (2006.01)
*B65D 75/32* (2006.01)
(Continued)

(52) U.S. Cl.
CPC .......... *B65D 75/366* (2013.01); *B65D 75/32* (2013.01); *A46B 15/0081* (2013.01);
(Continued)

(58) Field of Classification Search
CPC .. B65D 5/4204; B65D 73/0057; B65D 73/00; B65D 75/36; B65D 75/522;
(Continued)

(56) References Cited

U.S. PATENT DOCUMENTS 1,844,189 A * 2/1932 Stuart ...................... B65D 5/38
206/534
2,304,227 A * 12/1942 Zafarana ................ A45D 44/18
206/362.2
(Continued)

FOREIGN PATENT DOCUMENTS

CN     2790947     6/2006
CN   201634065    11/2010
(Continued)

OTHER PUBLICATIONS

First KR Office Action in corresponding KR Application No. 10-2013-7033976. KR.
(Continued)

*Primary Examiner* — J. Gregory Pickett
*Assistant Examiner* — Gideon Weinerth

(57) ABSTRACT

An oral care kit (1000) including a package (100), a toothbrush (200) positioned within the package and a backer card (300) comprising a window aperture (30). The oral care kit provides the user with the ability to view a portion of the toothbrush, such as the head (210), from both the front and rear of the package while maintaining the package in an enclosed state. In one embodiment of the invention, the package comprises a front cover (101) comprising a substantially transparent window portion (130) and a rear cover (102) comprising a substantially transparent window portion (120), the rear cover coupled to the front cover to form a receiving cavity (115). The backer card is positioned within the receiving cavity between the toothbrush and the rear cover so that the window portion of the rear cover, the window aperture (301) of the backer card, a portion of the toothbrush, and the window portion of the front cover are transversely aligned.

7 Claims, 6 Drawing Sheets

(51) Int. Cl.
  *B65D 73/00* (2006.01)
  *A46B 15/00* (2006.01)
  *A61C 17/22* (2006.01)

(52) U.S. Cl.
  CPC ... *A46B 15/0093* (2013.01); *A46B 2200/1066* (2013.01); *A61C 17/22* (2013.01); *B65D 73/00* (2013.01)

(58) Field of Classification Search
  CPC .. B65D 73/0092; B65D 75/366; B65D 75/32; B65B 5/02; A46B 15/0081; A46B 15/0093; A61C 17/22
  USPC ......... 206/361, 459.5, 461, 362.2, 368, 471, 206/362.3; 229/162.1, 162.3, 162.6, 229/162.7
  See application file for complete search history.

(56) References Cited

U.S. PATENT DOCUMENTS

| | | | | |
|---|---|---|---|---|
| 2,532,857 A * | 12/1950 | Ricciardi | ............... | B65D 25/54 206/0.815 |
| 2,557,794 A * | 6/1951 | Nicolle | ............... | B65D 75/322 156/210 |
| 2,931,494 A * | 4/1960 | Pfohl | ............... | B65D 73/0014 206/462 |
| 2,993,590 A * | 7/1961 | Denton | ............... | 206/469 |
| 3,011,629 A * | 12/1961 | Rohdin | ............... | B65D 73/0092 206/461 |
| 3,017,987 A * | 1/1962 | Moslo | ............... | B65D 25/54 220/665 |
| 3,047,143 A * | 7/1962 | Voigt | ............... | B65D 73/0057 206/467 |
| D197,737 S * | 3/1964 | Strongwater | ............... | D9/415 |
| 3,178,019 A * | 4/1965 | Fetzek | ............... | B65D 73/0092 206/464 |
| 3,220,543 A * | 11/1965 | McCord et al. | ............... | 206/362.2 |
| 3,307,693 A * | 3/1967 | Bittner | ............... | B65D 75/326 206/461 |
| 3,394,802 A * | 7/1968 | Hershaft | ............... | B65D 75/326 206/457 |
| 3,399,763 A * | 9/1968 | Stone | ............... | B65D 73/0057 206/462 |
| 3,432,380 A * | 3/1969 | Weber | ............... | B29C 44/0446 220/663 |
| 3,498,018 A * | 3/1970 | Gifford et al. | ............... | 53/433 |
| 3,621,996 A * | 11/1971 | Seyer | ............... | B65D 83/0088 206/463 |
| 3,730,335 A * | 5/1973 | Tarrson | ............... | B65D 5/5007 206/362.2 |
| 3,948,393 A * | 4/1976 | Lewi | ............... | B65D 73/0057 206/462 |
| 3,972,417 A | 8/1976 | Iten et al. | | |
| 4,091,927 A * | 5/1978 | Lunsford | ............... | 206/459.5 |
| 4,261,462 A * | 4/1981 | Wysocki | ............... | 206/463 |
| 4,466,534 A * | 8/1984 | Dunn | ............... | B65D 75/54 206/462 |
| 4,499,353 A * | 2/1985 | Shields | ............... | B65D 73/0057 206/470 |
| 4,804,984 A * | 2/1989 | Heuer | ............... | B65D 75/32 206/316.2 |
| 4,821,951 A * | 4/1989 | Franzoni | ............... | B65D 5/4204 229/162.1 |
| 4,842,141 A * | 6/1989 | Segal | ............... | B65D 73/0092 206/338 |
| 5,012,972 A * | 5/1991 | Nordstrom | ............... | B65D 5/4204 229/109 |
| 5,188,222 A * | 2/1993 | Pierce | ............... | B65D 75/32 206/301 |
| 5,209,354 A * | 5/1993 | Thornhill | ............... | B65D 43/163 206/461 |
| D336,040 S * | 6/1993 | Philippe | ............... | D9/415 |
| 5,379,886 A * | 1/1995 | Brauner | ............... | B65D 5/5286 206/216 |
| 5,407,066 A | 4/1995 | Grange | | |
| 5,505,301 A * | 4/1996 | Foley | ............... | A47K 1/09 206/362.2 |
| 5,579,288 A * | 11/1996 | Malloy | ............... | B65D 75/32 206/18 |
| 5,636,933 A | 6/1997 | Vizsolyi | | |
| 5,980,145 A | 11/1999 | Griffith | | |
| 6,010,462 A * | 1/2000 | Stoermer, III | ............... | B65B 9/042 206/210 |
| 6,039,495 A * | 3/2000 | Zimmerman | ............... | B42F 13/40 206/461 |
| D425,414 S * | 5/2000 | Baker | ............... | D9/415 |
| 6,059,106 A | 5/2000 | Baker et al. | | |
| 6,276,529 B1 | 8/2001 | Feehan, Jr. | | |
| 6,301,814 B1 | 10/2001 | Baxter | | |
| 6,345,716 B1 * | 2/2002 | Chapman | ............... | 206/471 |
| 6,513,655 B2 * | 2/2003 | Logan | ............... | B65D 75/366 206/467 |
| 6,564,940 B2 | 5/2003 | Blaustein et al. | | |
| 6,719,139 B1 * | 4/2004 | Foos | ............... | B29C 51/04 206/462 |
| 6,814,227 B2 * | 11/2004 | Seligman | ............... | A47G 1/12 206/0.82 |
| D501,791 S * | 2/2005 | Geiberger | ............... | D9/415 |
| 6,889,829 B2 | 5/2005 | Lev et al. | | |
| 6,986,424 B1 | 1/2006 | Morrison | | |
| 6,993,803 B2 | 2/2006 | Chan | | |
| 7,204,367 B2 * | 4/2007 | Bott | ............... | B65D 73/0092 206/219 |
| 7,213,709 B2 * | 5/2007 | Moskovich | ............... | B65D 73/0042 206/362.2 |
| 7,344,026 B2 * | 3/2008 | Melgaard | ............... | 206/349 |
| D566,541 S * | 4/2008 | Nanda | ............... | D9/415 |
| D584,160 S * | 1/2009 | Zimmermann | ............... | D9/415 |
| 7,475,775 B2 * | 1/2009 | Fattori | ............... | B65D 25/20 206/362.2 |
| D590,245 S * | 4/2009 | Nanda | ............... | D9/415 |
| D622,138 S * | 8/2010 | Winkler et al. | ............... | D9/415 |
| 7,861,856 B2 | 1/2011 | Rowe | | |
| 7,992,710 B2 * | 8/2011 | Jimenez | ............... | A61C 17/221 206/362.2 |
| 8,177,066 B2 * | 5/2012 | Tilton | ............... | B65D 73/0057 206/462 |
| D684,040 S * | 6/2013 | Bloch | ............... | D9/415 |
| D700,047 S * | 2/2014 | Bloch | ............... | D9/415 |
| D700,048 S * | 2/2014 | Bloch | ............... | D9/415 |
| D704,548 S * | 5/2014 | Demar | ............... | D9/415 |
| D781,138 S * | 3/2017 | Hubner | ............... | D9/415 |
| 2001/0032796 A1 | 10/2001 | Rubenstein | | |
| 2001/0054561 A1 | 12/2001 | Blaustein et al. | | |
| 2002/0088730 A1 * | 7/2002 | Galomb | ............... | B31B 41/00 206/459.5 |
| 2002/0100134 A1 | 8/2002 | Dunn et al. | | |
| 2003/0205492 A1 * | 11/2003 | Ferber et al. | ............... | 206/362.2 |
| 2005/0087464 A1 | 4/2005 | Brattesani et al. | | |
| 2005/0161313 A1 | 7/2005 | Sorrentino et al. | | |
| 2005/0218027 A1 * | 10/2005 | Lammers et al. | ............... | 206/467 |
| 2007/0040010 A1 | 2/2007 | Bauer | | |
| 2008/0035516 A1 * | 2/2008 | Lombardi et al. | ............... | 206/469 |
| 2009/0090643 A1 | 4/2009 | Fischer et al. | ............... | 206/361 |
| 2009/0158540 A1 | 6/2009 | Baertschi et al. | | |
| 2009/0178286 A1 | 7/2009 | Leventhal et al. | | |
| 2009/0229063 A1 | 9/2009 | Merl et al. | | |
| 2009/0236241 A1 | 9/2009 | Jimenez et al. | | |
| 2009/0307859 A1 | 12/2009 | Mottram et al. | | |
| 2010/0193392 A1 * | 8/2010 | Karow | ............... | B65D 73/0057 206/462 |
| 2011/0061779 A1 | 3/2011 | Tilgner | | |
| 2011/0068044 A1 | 3/2011 | Sorrentino et al. | | |
| 2011/0079529 A1 * | 4/2011 | Appelbaum | ............... | B65D 73/0057 206/462 |
| 2011/0139661 A1 * | 6/2011 | Ludwig | ............... | B29C 65/18 206/462 |
| 2012/0145567 A1 * | 6/2012 | Nguyen | ............... | B65D 75/326 206/63.5 |

(56) References Cited

U.S. PATENT DOCUMENTS

| | | | |
|---|---|---|---|
| 2013/0248388 A1* | 9/2013 | Jimenez | A46B 15/0085 206/214 |
| 2013/0256165 A1* | 10/2013 | Moskovich | B65D 75/322 206/362.3 |
| 2013/0327667 A1* | 12/2013 | Grabowski | B65B 5/04 206/438 |
| 2014/0008266 A1* | 1/2014 | Lee | B65D 75/368 206/581 |
| 2014/0166515 A1* | 6/2014 | Nguyen | B65D 75/367 206/368 |
| 2014/0231295 A1* | 8/2014 | Ponzini | B65B 5/04 206/462 |
| 2014/0339111 A1* | 11/2014 | Moskovich | B65D 75/366 206/362.3 |

FOREIGN PATENT DOCUMENTS

| | | |
|---|---|---|
| CN | 201634067 | 11/2010 |
| KR | 200362566 | 9/2004 |
| WO | WO 2004/112538 | 12/2004 |
| WO | WO 2006/020075 | 2/2006 |
| WO | WO 2009/116997 | 9/2009 |

OTHER PUBLICATIONS

International Search Report and the Written Opinion of the International Searching Authority issued in International Application PCT/US2011/038297 mailed Apr. 17, 2012.

\* cited by examiner

ORAL CARE KIT FOR DISPLAYING A PORTION OF A TOOTHBRUSH

CROSS-REFERENCE TO RELATED PATENT APPLICATIONS

The present application is a U.S. national stage application under 35 U.S.C. §371 of PCT Application No. PCT/US2011/038297, filed May 27, 2011. The disclosure of the above application is incorporated herein by reference.

FIELD OF THE INVENTION

The present invention relates generally to the field of oral care kits, and specifically to oral care kits that include a package and a toothbrush contained therein.

BACKGROUND OF THE INVENTION

In the commercialization of toothbrushes, the current trend is to package toothbrushes in blister packages. Because blister packages are typically formed of thin plastic films, blister packages often include a backer card contained therein on which product information is provided. While existing backer cards are helpful in relaying product information to the consumer, these backer cards completely block visibility of the toothbrush from the rear of the package. As a result, consumers are left to speculate as to the appearance and/or features located on the rear of the toothbrush. Thus, existing packages for toothbrushes are especially problematic when a toothbrush comprises features on both of its front and rear surfaces that can create commercial interest in the consumer.

BRIEF SUMMARY OF THE INVENTION

The present invention is directed to an oral care kit comprising a package, a toothbrush positioned within the package and a backer card comprising a window aperture. The oral care kit provides the user with the ability to view a desired portion of the toothbrush, such as the head, from both the front and rear of the package while maintaining the package in an enclosed state.

In one embodiment, the invention can be an oral care kit comprising: a blister package comprising a substantially transparent front cover and a substantially transparent rear cover coupled to the front cover to form a receiving cavity; a toothbrush comprising a handle and a head comprising a first surface and a second surface opposite the first surface, the toothbrush positioned within the receiving cavity; a backer card comprising a window aperture, the backer card positioned within the receiving cavity between the toothbrush and the rear cover; and wherein the head of the toothbrush is visible from outside of the package: (1) through the rear cover and the window aperture of the backer card; and (2) through the front cover.

In another embodiment, the invention can be an oral care kit comprising: a package having a longitudinal axis, the package comprising: a three-dimensionally contoured front cover comprising a substantially transparent window portion; and a rear cover comprising a substantially transparent window portion, the rear cover coupled to the three-dimensionally contoured front cover to form a receiving cavity; a toothbrush comprising a handle and a head positioned within the receiving cavity; a backer card comprising a window aperture, the backer card positioned within the receiving cavity between the toothbrush and the rear cover; and wherein the window portion of the rear cover, the window aperture of the backer card, the head of the toothbrush, and the window portion of the three-dimensionally contoured front cover are transversely aligned.

In yet another embodiment, the invention can be an oral care kit comprising: a package having a longitudinal axis, the package comprising: a front cover comprising a substantially transparent window portion; and a rear cover comprising a substantially transparent window portion, the rear cover coupled to the front cover to form a receiving cavity; a toothbrush comprising a handle and a head positioned within the receiving cavity; a backer card comprising a window aperture, the backer card positioned within the receiving cavity between the toothbrush and the rear cover; and wherein the window portion of the rear cover, the window aperture of the backer card, a portion of the toothbrush, and the window portion of the front cover are transversely aligned, wherein the window portion of the rear cover, the window aperture of the backer card, a portion of the toothbrush, and the window portion of the front cover are transversely aligned.

In still another embodiment, the invention can be an oral care kit comprising: a package comprising: a front cover comprising a substantially transparent window portion and a three-dimensional contour forming a receiving cavity; a backer card comprising a window aperture, the backer card coupled to the front cover to enclose the receiving cavity; a rear cover comprising a substantially transparent window portion enclosing the window aperture; a toothbrush positioned within the receiving cavity; and wherein a portion of the toothbrush is visible through: (1) the window portion of the rear cover and the window aperture of the backer card; and (2) the window portion of the front cover.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
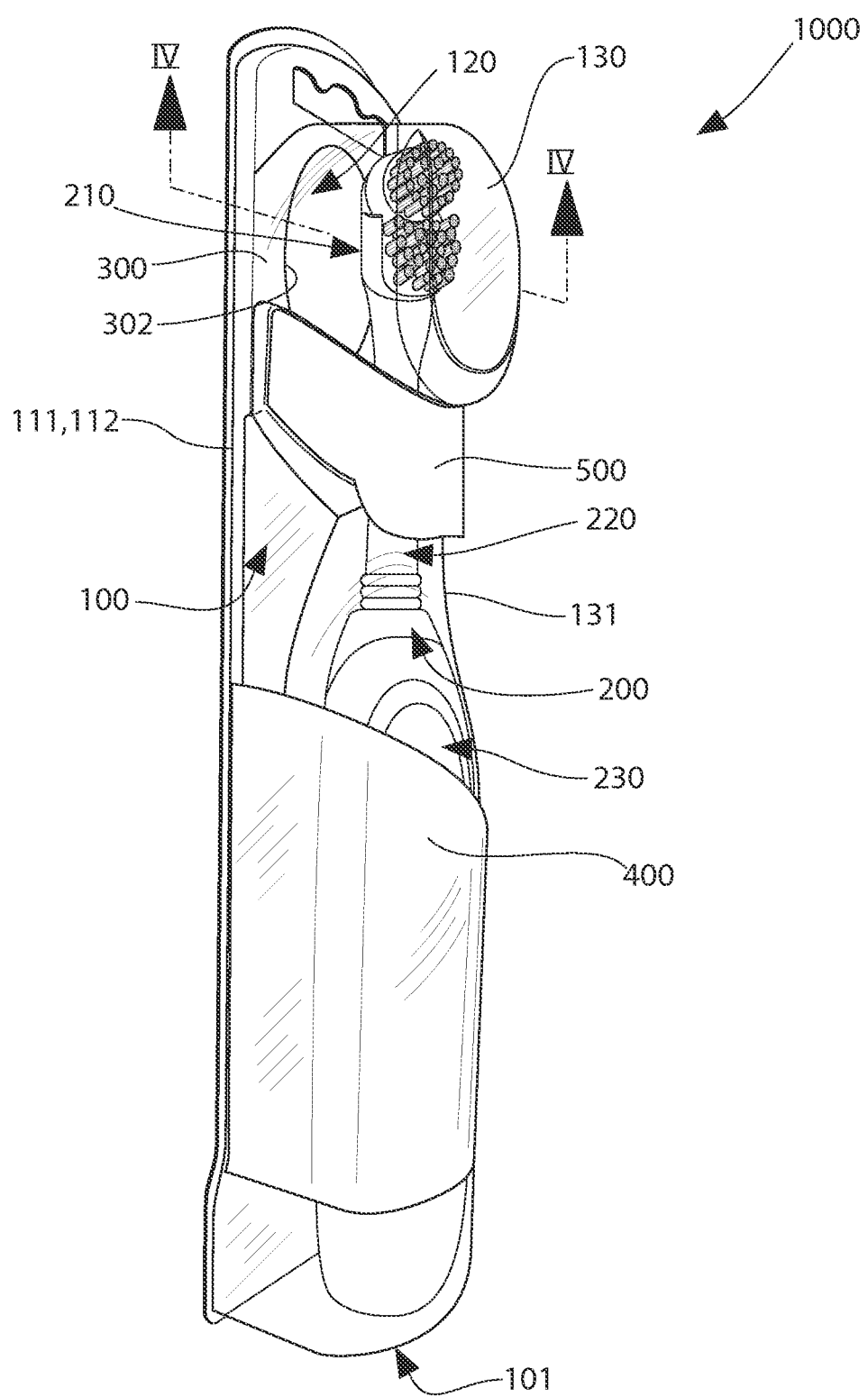
FIG. 1 is a perspective view of an oral care kit according to one embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Referring to FIGS. 1-5 concurrently, an oral care kit 1000 is illustrated according to one embodiment of the present invention. The oral care kit 1000 generally comprises a package 100, a toothbrush 200, a backer card 300, a sleeve 400, and a panel 500. In some embodiments, the sleeve 400 may include product information, marketing information, instructions, and/or other relevant information. In the embodiment as shown, the panel 500 is a sticker panel that is attached to a portion of the front cover of the package 100. The panel 500 may include graphics, logos, and/or other visual designs. The toothbrush 200, the backer card 300 and the sleeve 400 are disposed within the package 100. In the exemplified embodiment, the entirety of the toothbrush 200, the entirety of the backer card 300, and the entirety of the sleeve 400 are disposed in the package 100 such that the toothbrush 200, the backer card 300, and the sleeve 400 are sealed therein. However, in alternate embodiments, only a portion of the toothbrush 200, only a portion of the backer card 300 and/or only a portion of the sleeve 400 may be disposed within the package 100 while another portion of the toothbrush 200, the backer card 300, and/or the sleeve 400 protrudes therefrom. Similarly, in alternative embodiments, the entirety of the backer card 300 and the sleeve 400 may be outside of the package 100. In some embodiments, the backer card 300 may form the entirety or a portion of the rear cover of the package 100.

The oral care kit 1000 is exemplified in conjunction with the commercialization of a toothbrush 200. The invention, however, is not so limited. In alternate embodiments, other oral care implements can be used in conjunction with the oral care kit 1000, including tongue cleaners, tooth polishers, oral care material dispensers, and other oral care ansate implements. Moreover, while the toothbrush 200 is exemplified as a powered toothbrush, the toothbrush 200 may be a manual toothbrush in other embodiments of the invention.

As noted above, in the exemplified embodiment, the toothbrush 200 is a powered toothbrush. In certain embodiments, the toothbrush 200 comprises an oscillating tuft block 218 and a stationary tuft block 219. However, in certain other embodiments the oscillating tuft block 218 may move with a vibratory motion rather than an oscillating motion. Furthermore, in still other embodiments, the toothbrush 200 may comprise one or more movable tuft blocks and the stationary tuft block 219 may be omitted.

The toothbrush 200 generally comprises a head 210, a neck 220 and a handle 230. The handle 230 provides the user with a mechanism by which he/she can readily grip and manipulate the toothbrush 200. The handle 230 may be formed of many different shapes, sizes, materials and a variety of manufacturing methods that are well-known to those skilled in the art. If desired, the handle 230 may include a suitable textured grip made of soft elastomeric material. The handle 230 can be a single or multi-part construction.

The handle 230 transitions into the neck 220 at a distal end. While the neck 220 is illustrated as having has a smaller transverse cross-sectional area than the handle 230, the invention is not so limited. The neck 220 is the transition region between the handle 230 and the head 210 and can conceptually be considered as a portion of the handle 230. In this manner, the head 210 is connected to the distal end of the handle 230 (via the neck 220).

The head 210 generally comprises a front surface 211, a rear surface 212 and a peripheral surface 213. The front surface 211 and the rear surface 212 of the head 210 are opposite one another and can take on a wide variety of shapes and contours, none of which are limiting of the present invention. For example, the front and rear surfaces 211, 212 can be planar, contoured or combinations thereof. The rear surface 212 comprises a soft tissue cleanser 240. The soft tissue cleanser 240 is constructed of an elastomeric material, such as a thermoplastic elastomer, and comprises a plurality of protuberances 241 for engaging and/or massaging soft oral tissue. Details of the soft tissue cleanser are disclosed in U.S. Pat. No. 7,143,462, issued Dec. 5, 2006 to the assignee of the present application, the entirety of which is hereby incorporated by reference. Furthermore, while the head 210 is normally widened relative to the neck 220 of the handle 230, it could in some constructions simply be a continuous extension or narrowing of the handle 230.

The front surface 211 of the head 210 comprises a collection of tooth engaging elements 215 extending therefrom for cleaning and/or polishing contact with a user's teeth. While the collection of tooth engaging elements 215 is preferably suited for brushing teeth, the collection of tooth engaging elements 215 can also be used to polish teeth instead of or in addition to cleaning teeth. As used herein, the term "tooth engaging elements" is used in a generic sense to refer to any structure that can be used to clean, polish or wipe the teeth through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material preferably has a hardness property in the range of A8 to A25 Shore hardness. One preferred elastomeric material is styrene-ethylene/butylene-styrene block copolymer (SEBS) manufactured by GLS Corporation. Nevertheless, SEBS material from other manufacturers or other materials within and outside the noted hardness range could be used.

When the oral care kit 1000 is assembled for retail display (as shown in FIG. 1), at least a portion of the toothbrush 200 is visible from outside of the package 100 from both the front of the package 100 and the rear of the package 100 (discussed in greater detail below). As a result, surfaces of the portion of the toothbrush 200 that are opposite one another (i.e., 180° apart) can be viewed by the consumer without removing the toothbrush 200 from the package 100 or compromising the integrity of the package 200. Thus, improved visual display of the toothbrush 200 can be achieved in accordance with the present invention that allows the consumer to properly evaluate the contents of the oral care kit 1000 at the point of sale.

The package 100 extends along a longitudinal axis A-A. The package 100 may take on a wide variety of embodiments and may be of a wide variety of packaging types as is known in the art. In one embodiment, the package 100 is a blister package. The package 100 generally comprises a three-dimensionally contoured front cover 101 and a rear cover 102. The three-dimensionally contoured front cover 110 and the rear cover 102, in one embodiment, are thermoformed plastic films. Suitable thermoformed plastic films may be constructed of such material as polyethyleneterephtalate (PETA, PETG, PETGAG), polyvinylchloride (PVC), polypropylene (PP) or styrol-butadiene-blockcopolymer (SBS), preferred PVC. Other suitable materials of construction for the thermoformed plastic film include, without limitation, renewable primary products, for example of cornstarch, sugar (polyhydroxybutyrat/-valerat), cellulose diacetat, cellulose nitrate, polyactid (PLA), and polyhydroxybutyrat (PHB).

The front cover 101 is three-dimensionally contoured so that a receiving cavity 115 (FIGS. 4-5) is formed between the front cover 101 and the rear cover 102 when the front cover 101 and the rear cover 102 are coupled together. In one embodiment, the front cover 101 is three-dimensionally contoured to generally correspond to the general shape of the oral care product that is to be disposed therein, which in the exemplified embodiment is the toothbrush 200. In alternate embodiments, a front cover may be used that is not three-dimensionally contoured if desired. For example, in an alternate embodiment, the front cover may assume a generally rectangular box shape. In the exemplified embodiment, the three-dimensionally contoured front cover 101 comprises a perimeter portion 111 while the rear cover 102 comprises a perimeter portion 112. The perimeter portion 111 of the front cover 101 circumferentially surrounds a three-dimensionally contoured portion 131 of the front cover 110. Similarly, the perimeter portion 112 of the rear cover 102 circumferentially surrounds a panel portion 103 of the rear cover 102. The perimeter portion 111 of the front cover 101 provides a mating structure for coupling to the perimeter portion 112 of the rear cover 120. The perimeter portion 111 of the front cover 101 can be coupled to the perimeter portion 112 of the rear cover 120 via a thermal weld, adhesive, interference fit, tab, tape, combinations thereof, or any other suitable technique as would be understood by those of skill in the art.

The front cover 101 comprises a window portion 130. As discussed below, the window portion 130 of the front cover 101 is transversely aligned with the portion of the toothbrush 200 that is desired to be displayed to the consumer, which in the exemplified embodiment is the head 210.

In the exemplified embodiment, the entirety of the front cover 101 and the entirety of the rear cover 102 are substantially transparent, thereby allowing visibility therethrough. However, in alternate embodiments, only a portion of the front cover 101 and a portion of the rear cover 102 may be substantially transparent so as to form the window portions 120, 130 (discussed in greater detail below). In embodiments where only a portion of the front cover 110 and a portion of the rear cover 102 are substantially transparent, the substantially transparent portions 120, 130 will preferably be transversely aligned with a window aperture 301 of the backer card 300 (discussed in greater detail below) and the portion of the toothbrush 200 desired to be displayed to the consumer. As used herein, the term "transparent" includes materials that allow a user to see through the material, even if the material is colored or includes a small degree of translucency.

The panel portion 103 of the rear cover 102, in the exemplified embodiment, is a substantially planar panel comprising a planar top surface 122 and a planar bottom surface 123. Of course, in other embodiments, the panel portion 103 of the rear cover 102 may also be three-dimensionally contoured. In certain alternate embodiments in which the rear cover 102 is three-dimensionally contoured, the rear cover 102 may form a cavity that forms a portion of the receiving cavity 115 in which a portion of the toothbrush 200, a portion of the backer card 300, and/or a portion of the sleeve 400 is disposed.

The panel portion 103 of the rear cover 102 further comprises a closure panel 104. The closure panel 104 is provided as a mechanism for opening and closing the package 100 so that the toothbrush 200 can be removed therefrom. More specifically, the closure panel 104 is alterable between an open position (not illustrated) in which the toothbrush can be removed from the package 100 and a closed position (FIGS. 2 and 5) in which the receiving cavity 115 is substantially enclosed. In the exemplified embodiment, the closure panel 104 is formed by creating a transverse slit 105 through the panel portion 103 and two pre-weakened areas 106A, 106B extending longitudinally therefrom in a spaced apart manner. Thus, when a user desires to alternate the closure panel 104 from the closed position to the open position in order to remove the toothbrush 200 from the package 100, he/she first grasps the free end of the closure panel 104 (which is the edge of the closure panel formed by the slit 105). The user then pulls the free edge of the closure panel 104 outwardly and away from the bottom surface 123 of the rear cover 102, thereby breaking the pre-weakened areas 106A, 106B to create a living hinge in area 107 of the rear cover 102. The pre-weakened areas 106A, 106B can be formed by forming perforations in the rear cover 102, scoring the rear cover 102, pre-creasing the rear cover 102, combinations thereof, and/or otherwise comprising the integrity of the rear cover 102 in a controlled manner through the use of chemical energy, thermal energy, mechanical energy, or combinations thereof.

The rear cover 103 further comprises a window portion 120 that, as discussed below, facilitates visibility of a portion of the toothbrush 200 from the rear of the package 100. The window portion 120, in the exemplified embodiment, protrudes from the top surface 122 of the rear cover 102. The invention, however, is not so limited and in alternate embodiments, the window portion 120 may not protrude from the top surface 122 of the rear cover 102 and/or may merely be a contiguous portion of the panel portion 103.

The window portion 120 comprises an upstanding wall 124 that forms a closed perimeter geometry. In the exemplified embodiment, the closed perimeter geometry (and thus the shape of the window portion 120) is oval. The invention, however, is not limited to any particular shape for the window portion 120. Nonetheless, as discussed below, in one embodiment, it is preferred that the window portion 120 of the rear cover 102 has a shape and size that corresponds to a shape and size of the window aperture 301 of the backer card 300. The window portion 120 of the rear cover 102 further comprises a substantially flat panel 125 connected to a top edge 126 of the upstanding wall 124. In other embodiments, however, the panel 125 of the window portion 120 may be contoured either convexly or concavely as desired. As discussed in greater below, when the oral care kit 1000 is assembled, the window portion 120 of the rear cover 102 extends into the window aperture 301 of the backer card 300 to retain the backer card 300 in place within the receiving cavity 115.

The backer card 300, in the exemplified embodiment, is a flat panel. In certain other embodiments, however, the backer card 300 may be three-dimensionally contoured. The backer card 300 may comprise product information. In such embodiments, the backer card 300 comprises indicia that provides information to a consumer about the toothbrush 200 (or other oral care product disposed within the package 100). The indicia on the backer card 300 may include instructions, logos, advertisements, and/or other marketing information. All or a portion of the backer card 300 can be opaque so that product information can be effectively conveyed to the consumer. However, such opaqueness can block effective viewing of the toothbrush 200 disposed within the package 100.

Figures 3A, 3B:
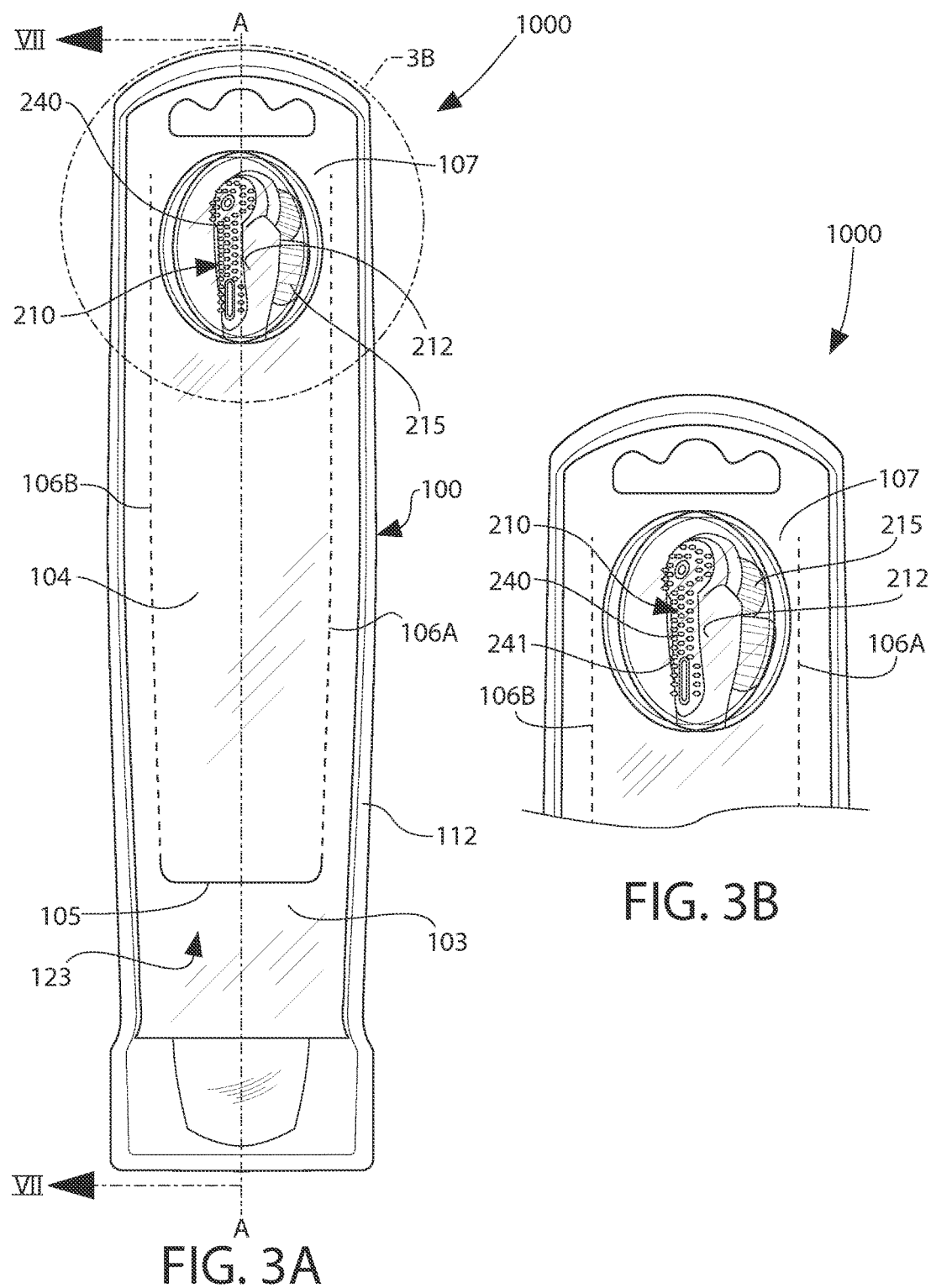
FIG. 3A is a plan rear view of the oral care kit of FIG. 1.
FIG. 3B is a close-up view of area 3B of FIG. 3A.

In order to ensure that the desired portion of the toothbrush 200 is adequately displayed despite the inclusion of the backer card 300, the backer card 300 comprises the window aperture 301. The window aperture 301 forms a passageway through the backer card 300, thereby providing a viewing window when transversely aligned with the window portion 120 of the rear cover 102 that allows the desired portion of the toothbrush 200 to be viewed from the rear of the package 100 (as shown in FIGS. 3A-B). The window aperture 301 is formed by an inner edge 302 of the backer card 300 that forms a closed perimeter. When the oral care kit 1000 is assembled, the upstanding wall 124 of the window portion 120 of the rear cover 102 and the inner edge 302 of the backer card 300 retains the backer card 300 in place within the receiving cavity 115. While the window aperture 301 is illustrated as being oval in shape, it is contemplated that in other embodiments, the window aperture 301 may assume other appropriate geometric shapes, such as rectangular, triangular, circular, or the like.

The backer card 300 can be a single layer or a multi-layer laminate. The back card 300 can be constructed of plastic, film, paperboard, combinations thereof, or any other suitable material. While the backer card 300 is flexible in certain embodiments, in other embodiments the backer card 300 may be rigid or semi-rigid. In addition, in embodiments where only the head 210 (or other desired portion) is visible from outside of the rear of the package 100, a portion of the rest of the toothbrush 200 may not be visible from outside of the rear of the package 100. In such embodiments, the portion of the toothbrush 200 that may not be visible from outside of the rear of the package 100 may be one half, one third, one quarter, or the entirety of the toothbrush handle 230 (which may include neck 220).

Figure 2:
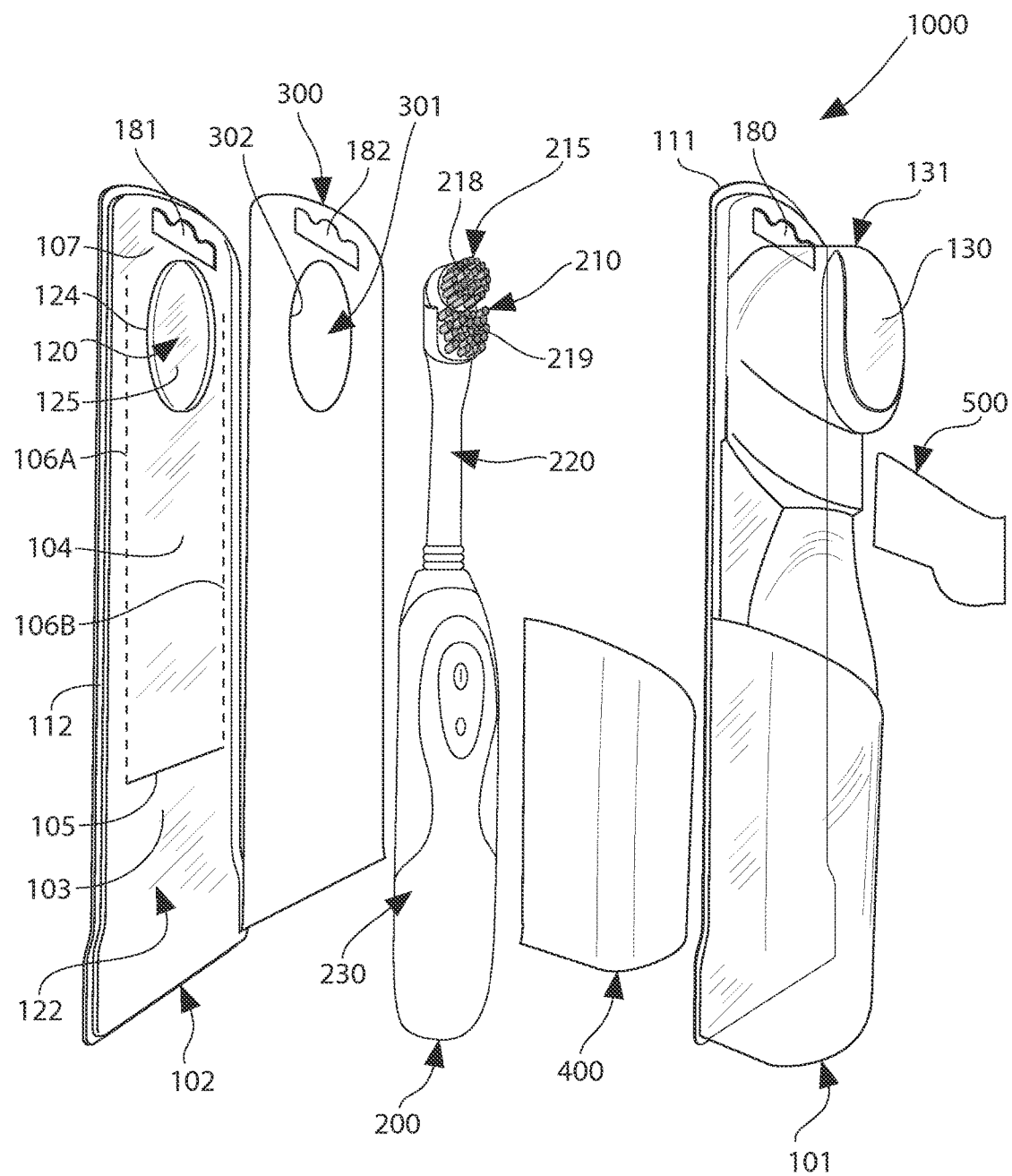
FIG. 2 is a perspective view of the oral care kit of FIG. 1 in a disassembled state.
Figure 4:
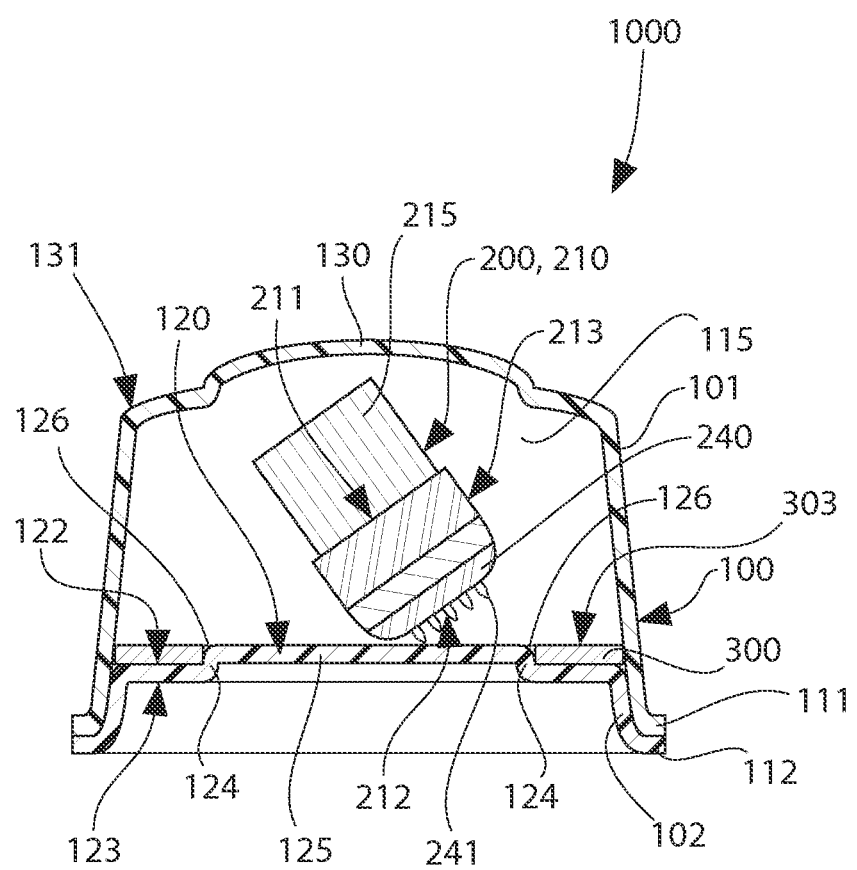
FIG. 4 is a transverse cross-sectional view of the oral care kit of FIG. 1 taken along line IV-IV of FIG. 1.
Figure 5:
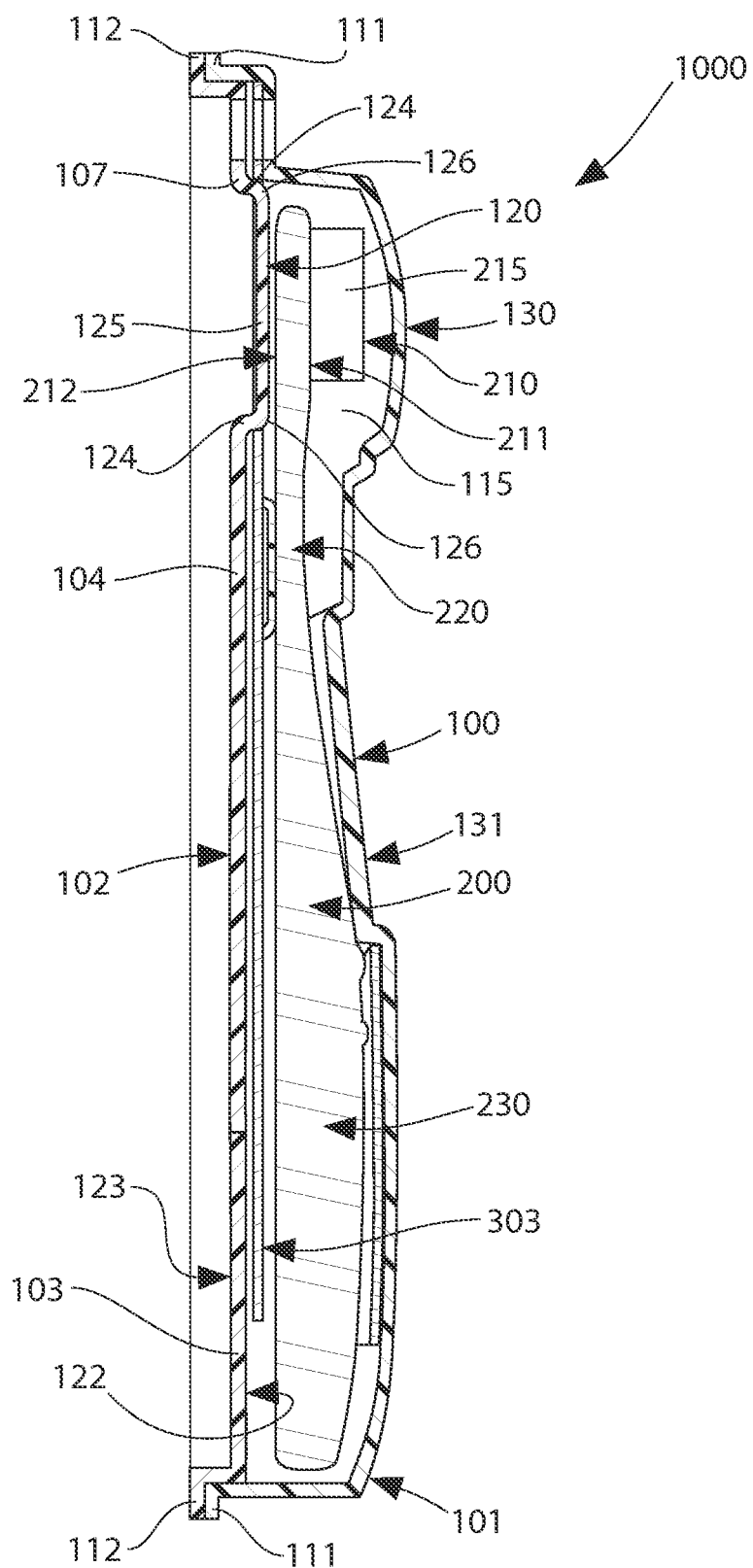
FIG. 5 is a longitudinal cross-sectional view of the oral care kit of FIG. 1 taken along line VII-VII of FIG. 3A.

Referring now to FIGS. 2, 4 and 5 concurrently, the oral care kit 1000 will be further described in its assembled state. When the oral care kit 1000 is assembled, the toothbrush 200 and the backer card 300 are positioned within the receiving cavity 115. More specifically, the backer card 300 is positioned adjacent the top surface 122 of the rear cover 102 of the package 100. Thus, the backer card 300 is positioned between the rear cover 102 of the package 100 and the toothbrush 200. Furthermore, when assembled and the closure panel 104 of the rear cover 102 is in the closed position, the window portion 120 of the rear cover 102 extends into the window aperture 301 of the backer card 300. As such, structural interference between the upstanding wall 124 of the window portion 120 of the rear cover 102 and the inner edge 302 of the backer card 300 that forms the window aperture 301 assists in retaining the backer card 300 in place within the receiving cavity 115. Thus, the window aperture 301 of the backer card 300 is retained in transverse alignment with the window portion 120 of the rear panel 102. Because the head 210 (or other desired portion) of the toothbrush 200 is also in transverse alignment with the window portion 120 and the window aperture 301, the head 210 (or other desired portion) of the toothbrush 200 is visible from outside of the rear of the package 100, even when the package 100 is sealed. In the exemplified embodiment, such visibility allows a potential customer to clearly and adequately inspect/view the soft tissue cleaner 240 on the rear surface 212 of the head 210 (see FIGS. 3A-B).

Furthermore, the window portion 130 of the front cover 130 is also in transverse alignment with the head 210 (or other desired portion) of the toothbrush 200 (and also consequently with the window portion 120 and the window aperture 301). As a result, the head 210 (or other desired portion) of the toothbrush 200 is simultaneously visible from outside of the front of the package 100, even when the package 100 is sealed. In the exemplified embodiment, such visibility allows a potential customer to clearly and adequately inspect/view the tooth engaging elements 215 on the front surface 211 of the head 210 (see FIG. 1). Thus, the present invention affords the potential consumer with the ability to view the head 210 (or other desired portion) of the toothbrush 200 from viewing angles that are 180° apart.

The ability to properly view the head 210 of the toothbrush 200 is further facilitated by the fact that the package 100 is configured so that the toothbrush 200 is mounted within the receiving cavity 115 so that the front and rear surfaces 211, 212 of the head 210 of the toothbrush 200 are at an oblique angle relative to a front surface 303 of the backer card 300 (shown in FIG. 4). Such mounting of the toothbrush 200 can be achieved using properly oriented retaining channels or other retaining structures.

The window portion 120 of the rear cover 102 is located within the closure panel 104. By locating the window portion 120 of the rear cover 102 within the closure panel 104, the window portion 120 of the rear cover 102 is withdrawn from the rear cover 102 during opening of the package 100 so as to not extend into the window aperture 301 of the backer card 300 when the closure panel 104 is in the open position. As a result, the backer panel 300 can be more easily removed so as to not prohibit or obstruct removal of the toothbrush 200 from the package 100.

Referring now to FIGS. 1 and 2 concurrently, the front cover 101 further comprises a hanger aperture 180 at a top end thereof. The rear cover 102 also has a corresponding hanger aperture 181 at a top end thereof. The backer panel 300 also comprises such a hanger aperture 182 at a top end thereof. When the oral care kit 1000 is assembled, the hanger apertures 180-182 are aligned so as to form a passageway through the package 100 which may be used for hanging the oral care kit 1000 for display in a retail store.

Figure 6:
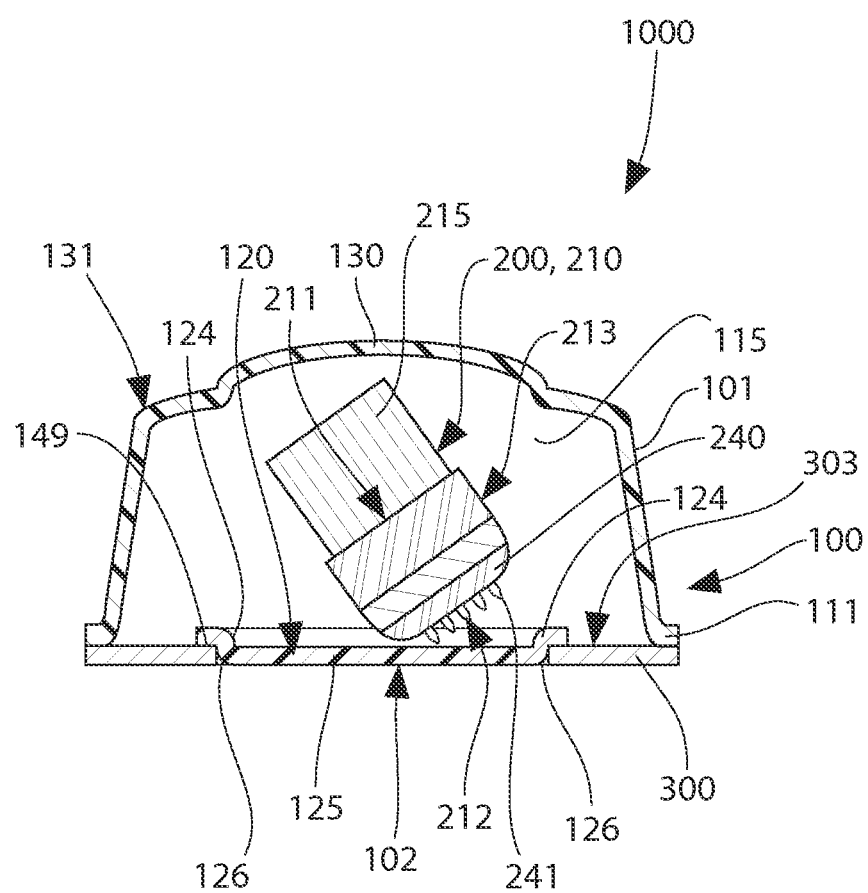
FIG. 6 is a transverse cross-sectional view of an oral care kit according to another embodiment of the present invention.

In some embodiments of the invention, such as the embodiment illustrated in FIG. 6, the backer card 300 can be sized appropriately to be coupled directly to the three dimensionally contoured front cover 101 so that the combination of the backer card 300 and the front cover 101 substantially enclose the receiving cavity 115. In one such embodiment, a perimeter portion of the backer card 300 will be coupled to a perimeter portion of the front cover. Such coupling can be achieved through the use of an adhesive, a thermal weld, fasteners, combinations thereof, or any other means known in the art. In such an embodiment, the backer card 300 can conceptually be considered as part of the package 100 of the oral care kit 1000.

As with the embodiments exemplified and discussed above with respect to FIGS. 1-5, the backer card 300 will comprise the window aperture 301. However, the window aperture 301 of the backer card 300 will be enclosed by the window portion 120 of the rear cover 102, which may be located inside or outside of the receiving cavity 115. The rear cover 102 may be directly coupled to the backer card 300 using any of the means discussed above. In the exemplified embodiment of FIG. 6, the rear cover 102 is located within the receiving cavity 115 and directly coupled to the top surface 303 of the backer card 300 so that the window portion 120 of the rear cover 102 extends downwardly into the window aperture 301. As a result, the rear cover 102 can not be easily dislodged and/or tampered with to expose the toothbrush 200.

In such an embodiment, the rear cover 102 may be substantially reduced in size so as to include only the window portion 120. In a further embodiment, the rear cover 102 may include an annular flange 149 surrounding the window portion 120 for facilitating coupling to the backer card 102. It is to be understood that the structural details discussed above with regards to FIGS. 1-5 are also applicable to the oral care kit 1000 of FIG. 6.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care kit comprising:
   (i) a package comprising:
      (a) a front cover comprising
         a perimeter portion,
         a substantially transparent window portion and
         a three-dimensional contour forming a receiving cavity,
      (b) a backer card comprising
         a front surface,
         a back surface,
         a perimeter portion, and
         a window aperture defined by an inner edge of the backer card that forms a closed perimeter,
         wherein the backer card's perimeter portion contacts the front cover's perimeter portion to enclose the receiving cavity, and
      (c) a substantially transparent rear window coupled to the backer card and extending into the window aperture of the backer card, the rear window comprising
         an annular flange for facilitating coupling of the window to the backer card, wherein the annular flange contacts the front surface of the backer card, and
         an upstanding wall that contacts the inner edge of the backer card; and
   (ii) a toothbrush comprising a handle, the toothbrush positioned within the receiving cavity;
   wherein a portion of the toothbrush is visible through: (1) the window; (2) the window aperture of the backer card; and (3) the window portion of the front cover, and
   wherein a portion of the handle is not visible through the rear cover.

2. The oral care kit according to claim 1 wherein the rear window, the window aperture of the backer card, the portion of the toothbrush, and the window portion of the front cover are transversely aligned.

3. The oral care kit according to claim 1 wherein the backer card is opaque.

4. The oral care kit according to claim 1 wherein the backer card is constructed of a paperboard material.

5. The oral care kit according to claim 1 wherein the front cover is a thermoformed thin plastic film.

6. The oral care kit according to claim 1 wherein the portion of the handle is one of: one half, one third, one quarter, and entirety of the handle.

7. The oral care kit according to claim 1 wherein the rear window further comprises a substantially planar portion.

* * * * *